United States Patent [19]

Kappler et al.

[11] 4,142,048
[45] Feb. 27, 1979

[54] PRODUCTION OF TRIS-(2-HYDROXYARYL) ESTERS OF CYANURIC ACID

[75] Inventors: Ulrich Kappler, Cologne; Rudolf Sundermann, Leverkusen, both of Fed. Rep. of Germany

[73] Assignee: Bayer Aktiengesellschaft, Leverkusen, Fed. Rep. of Germany

[21] Appl. No.: 657,920

[22] Filed: Feb. 13, 1976

[30] Foreign Application Priority Data

Mar. 6, 1975 [DE] Fed. Rep. of Germany ....... 2509780

[51] Int. Cl.² ........................................... C07D 251/30
[52] U.S. Cl. ........................................................ 544/219
[58] Field of Search .................. 260/248 CS; 544/219

[56] References Cited

U.S. PATENT DOCUMENTS

| 3,245,992 | 4/1966 | Dexter et al. | 260/248 |
| 3,530,127 | 9/1970 | Biland et al. | 260/248 |
| 3,763,157 | 10/1973 | Suryanarayana et al. | 260/248 |
| 3,775,411 | 11/1973 | Brunetti | 260/248 |
| 3,789,021 | 1/1974 | Suryanarayana et al. | 260/248 |

FOREIGN PATENT DOCUMENTS 1419632 12/1975 United Kingdom ..................... 544/219

Primary Examiner—John M. Ford
Attorney, Agent, or Firm—Sprung, Felfe, Horn, Lynch & Kramer

[57] ABSTRACT

Tris-(2-hydroxyaryl) esters of cyanuric acid, useful as cross-linking agents and UV absorbers, of the formula

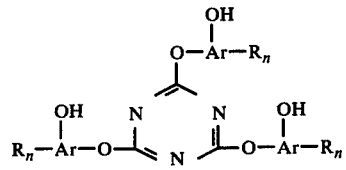

wherein

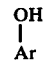

is an aromatic radical with a hydroxyl group in the 2-position to the ether oxygen, R is alkyl, phenyl, halogen, nitro, hydroxyl, alkoxy or phenoxy, and n is 0 or 1 or is 2, 3 or 4 in which case one R has the above-defined meaning and the or each further radical R is alkyl, the radicals R optionally being different.

9 Claims, No Drawings

PRODUCTION OF TRIS-(2-HYDROXYARYL) ESTERS OF CYANURIC ACID

BACKGROUND

This invention relates to new tris-(2-hydroxyaryl) esters of cyanuric acid and a process for their preparation.

Tris-(2-hydroxyaryl) esters of cyanuric acid have not been disclosed hitherto. According to C.R. Acad. Sc. Paris, Volume 271, Series C, pages 1599–1601, the reaction of pyrocatechol with cyanogen bromide in the presence of triethylamine gives a mixture of compounds from which it was possible to isolate 2,2'-dicyanato-diphenylimino-carbonate, whilst the reaction of tetrachloro- or tetrabromo-pyrocatechol with 1 or 2 mols of cyanogen bromide and triethylamine gives o-phenyleneimino-carbonate.

SUMMARY

It has now been found, surprisingly, that tris-(2-hydroxyaryl) esters of cyanuric acid are obtained when 1,2-dihydroxyaryl compounds are reacted with cyanogen halide in the presence of a solvent and of a hydrogen halide acceptor.

The invention therefore relates to tris-(2-hydroxyaryl) esters of cyanuric acid of the formula

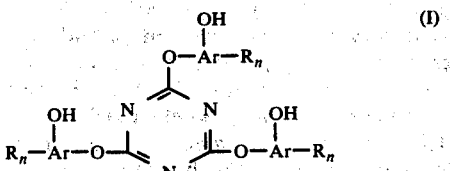

in which

denotes an aromatic radical with a hydroxyl group in the 2-position to the ether oxygen, R represents alkyl, phenyl, halogen, the nitro group, the hydroxyl group or an alkoxy or phenoxy group and n represents one of the numbers 0 or 1 or represents one of the numbers 2, 3 or 4, in which case one radical R then has the abovementioned meaning and the further radical or radicals R represent alkyl and can also be different.

The new tris-(2-hydroxyaryl) esters of the cyanuric acid of the formula I can be obtained according to the invention when 1,2-dihydroxyaryl compounds of the formula

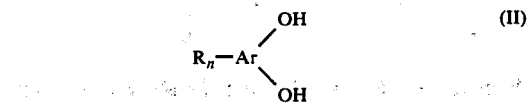

in which

Ar denotes an aromatic radical and

R and n have the abovementioned meaning, are reacted with cyanogen halide in the presence of a solvent and of a hydrogen halide acceptor.

DESCRIPTION

In general, the process according to the invention is carried out in a temperature range between −40° C. and +65° C., preferably in a temperature range between −5° and +20° C.

The cyanogen halides which can be used are, above all, cyanogen chloride and cyanogen bromide, which are readily accessible industrially, and especially cyanogen chloride.

Examples of solvents which may be mentioned are: aliphatic, cycloaliphatic, araliphatic and aromatic hydrocarbons as well as mixtures thereof, for example ligroin, cyclohexane, benzene, toluene and the xylenes; aliphatic, cycloaliphatic, araliphatic and aromatic halogenated hydrocarbons, for example methylene chloride, ethylene chloride, chlorobenzene and dichlorobenzene; aliphatic and aromatic nitro hydrocarbons, for example nitromethane and nitrobenzene; aliphatic and cyclic ethers, for example diethyl ether, isopropyl ether, diisobutyl ether, tetrahydrofurane and dioxane; lower aliphatic alcohols, such as methanol, ethanol, propanol, isopropanol and butanol; aliphatic ketones, for example acetone, diethyl ketone and methyl ethyl ketone; esters of aliphatic carboxylic acids with lower aliphatic alcohols, for example formic acid esters and acetic acid esters, such as methyl acetate and ethyl acetate, butyl acetate and amyl acetate; carboxylic acid amides, for example dimethylformamide and dimethylacetamide; and also water and solutions and mixtures of water with other solvents, especially those mentioned above, as well as mixtures and solutions of the solvents, especially the abovementioned solvents, with and in one another.

Preferred solvents are water, lower aliphatic alcohols with up to 6 carbon atoms, aromatic hydrocarbons, aliphatic chlorinated hydrocarbons and mixtures thereof; especially toluene, methylene chloride, isopropanol, water and a mixture of isopropanol/water and methylene chloride/water.

Hydrogen halide acceptors which can be used for the process according to the invention are: aliphatic and aliphatic-aromatic tertiary amines, such as trimethylamine, triethylamine and dimethylaniline; and alcoholates of the alkali metals and alkaline earth metals (such as lithium, sodium, potassium, magnesium and calcium) and lower aliphatic alcohols with up to 6 carbon atoms, such as methanol, ethanol, propanol, isopropanol, isobutanol and tert. butanol.

According to one variant of the process according to the invention, the reaction can be carried out in a purely organic medium in the presence of the abovementioned hydrogen halide acceptors.

According to a second variant of the process according to the invention, the reaction is carried out in the presence of water or of water and an organic solvent.

If water, water-containing solvent mixtures or lower aliphatic alcohols are used as the solvents in the process according to the invention, the oxides, hydroxides, bicarbonates and carbonates of the alkali metals and alkaline earth metals, preferably sodium hydroxide and potassium hydroxide, sodium bicarbonate and potassium bicarbonate and sodium carbonate and potassium carbonate, can also be used as hydrogen halide acceptors.

A large number of 1,2-dihydroxyaryl compounds, which can be used in the process according to the invention, are known; in general, they correspond to the general formula

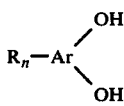

(II)

in which Ar, R and n have the abovementioned meaning.

Aromatic radicals which may be mentioned are those which have 6 to 14, preferably up to 10, carbon atoms in the ring system; preferred possible radicals are phenyl, naphthyl and phenanthryl, especially phenyl.

Alkyl radicals which may be mentioned are straight-chain and branched alkyl radicals with up to 9, especially up to 4, carbon atoms, preferably methyl, ethyl, propyl, isopropyl, butyl, isobutyl and tert.-butyl.

Halogens which may be mentioned are fluorine, chlorine, bromine and iodine, preferably chlorine and bromine.

Possible alkoxy groups are alkoxy groups with the scope of meanings mentioned above for alkyl.

Compounds of the formula II which may be mentioned are, in particular, compounds of the formula

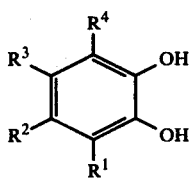

(III)

in which $R^1$ and $R^2$ are different and represent hydrogen, alkyl, phenyl, halogen, the nitro group, the hydroxyl group or an alkoxy or phenoxy group, and in each case only either $R^1$ or $R^2$ has a meaning other than hydrogen or alkyl, and $R^3$ and $R^4$ are identical or different and represent hydrogen or alkyl.

Preferred compounds of the formula II are pyrocatechol, mono-, di-, tri- and tetra-alkyl-substituted pyrocatechols and pyrocatechols, alkyl pyrocatechols and phenyl pyrocatechols which are substituted in the 3-position or 4-position by hydroxyl, alkoxy, phenoxy, chlorine, bromine and nitro.

Furthermore, 1,2-dihydroxynaphthalene, 2,3-dihydroxynaphthalene and o-dihydroxyphenanthrenes may be mentioned as preferred compounds of the formula II.

The process according to the invention is explained by the equation which follows, using pyrocatechol as an example.

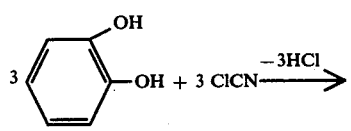

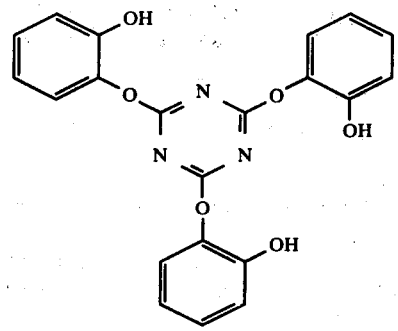

In the process according to the invention, the 1,2-dihydroxyaryl compound, the cyanogen halide and the base can be employed in a stoichiometric ratio, based on the hydroxyl group to be reacted. However, it is generally advantageous to use an excess of cyanogen halide and this excess can be up to 400%. Preferably, an excess of up to 300, especially up to 200% is used.

An excess of the hydrogen halide acceptor also does not have an adverse effect in the process according to the invention. The excess can be up to 300, preferably up to 200 and especially up to 150% of the stoichiometrically required amount.

In general, the process according to the invention is carried out in such a way that the 1,2-dihydroxyaryl compounds and the cyanogen halide are suspended and/or dissolved in the solvent and the hydrogen halide acceptor, which, if appropriate, is suspended and/or dissolved in water or an organic solvent, is added dropwise. However, it is also possible initially to introduce the 1,2-dihydroxyaryl compound together with the hydrogen halide acceptor in the solvent and then to add the cyanogen halide, which is dissolved in a solvent, if appropriate. Furthermore, the 1,2-dihydroxyaryl compound can be initially introduced in solution and/or suspended and the cyanogen halide and the hydrogen chloride acceptor can be added simultaneously, if appropriate in solution and/or suspension.

In particular, the new tris-(2-hydroxyaryl) esters of cyanuric acid of the formula I can correspond to

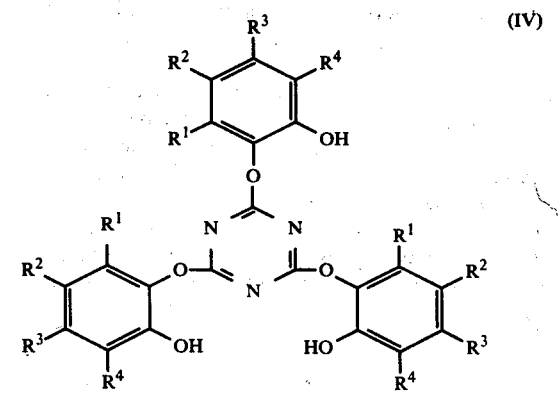

(IV)

in which $R^1$, $R^2$, $R^3$ and $R^4$ have the abovementioned meaning.

It is pointed out that when asymmetrically substituted compounds of the general formula III are used, the compounds which can be obtained by the process according to the invention do not have to correspond to the formula IV, since, in this case, mixtures of the compound corresponding to the formula IV and the possible structural isomers thereof can be obtained and, in some cases, for kinetic or energy reasons, the isomer corresponding to the formula IV can be present in only a very small amount.

For example, when 4-tert.-butyl-pyrocatechol is used three further isomers, for example the bis-(2-hydroxy-4-tert.-butylphenyl)-(2-hydroxy-5-tert.-butylphenyl) ester of cyanuric acid, can be formed in addition to the tris-(2-hydroxy-4-tert.-butylphenyl) ester of cyanuric acid.

The tris-(2-hydroxyaryl) esters of cyanuric acid, which can be obtained according to the process of the invention, are valuable intermediate products for plastics and are suitable for example, as crosslinking agents and can also be used as UV absorbers or antioxidants (see German Published Applications 2 155 453 and 2 307 777; U.S. Pat. No. 3,729,471). They are useful as starting phenols for the preparation of polyesters including polycarbonates as homopolymers or copolymers (see U.S. Pat. No. 3,739,035, German Published Specification 2 157 696). Furthermore, they can be reacted with cyanuric chloride to polyethers (see U.S. Pat. No. 3,297,639) and can be polymerized according to German Auslegeschrift 1 190 184.

EXAMPLE 1

11.0 g (0.1 mol) of pyrocatechol are initially introduced into 100 ml of toluene. After adding 11.1 g (0.105 mol) of triethylamine, 5.3 ml (0.105 mol) of cyanogen chloride are added dropwise, whilst stirring and cooling, at a temperature in the range from −5° to 0° C. When the addition of cyanogen chloride is complete, the mixture is stirred for a further 2 hours at room temperature. The inorganic salts are filtered off and rinsed with a large amount of toluene. The combined toluene filtrates are then washed with water until free from chloride. After distilling off the toluene from the toluene solution, an oil remains as the residue and this solidifies after some time. After recrystallisation from acetone, 9.5 g (70% of theory) of the tris-(2-hydroxyphenyl) ester of cyanuric acid are obtained as colourless crystals with a melting point of 205°–207° C.

EXAMPLE 2

11.0 g (0.1 mol) of pyrocatechol are initially introduced into 100 ml of toluene. After adding 5.3 ml (0.105 mol) of cyanogen chloride, 11.1 g (0.105 mol) of triethylamine are allowed to run in dropwise, whilst cooling and stirring and the mixture is then stirred for a further 2 hours at room temperature. The resulting reaction mixture is then worked up as described in Example 1. 8.7 g (64% of theory) of the tris-(2-hydroxyphenyl) ester of cyanuric acid are obtained.

EXAMPLE 3

55 g (0.5 mol) of pyrocatechol are dissolved in a mixture of 500 ml of methylene chloride and one liter of water. The mixture is cooled to 0° C. and 75 ml (1.5 mols) of cyanogen chloride are added. Whilst stirring and cooling, 53 g (0.5 mol) of $Na_2CO_3$, dissolved in 200 ml of water, are added dropwise, at a temperature between 0° and 10° C., at such a rate that a pH value of 8 is always maintained. 700 ml of N NaOH are then added slowly dropwise. After standing overnight at room temperature, the reaction product which has precipitated is filtered off. After recrystallisation from acetone, 54 g (80% of theory) of the tris-(2-hydroxyphenyl) ester of cyanuric acid are obtained as a colourless powder with a melting point of 205°–207° C.

EXAMPLE 4

55 g (0.5 mol) of pyrocatechol are dissolved in 200 ml of water and 500 ml of N NaOH are then added, whilst passing nitrogen through the solution. The mixture is then cooled to about 0° C. and 30 ml of cyanogen chloride, dissolved in 100 ml of isopropanol, are added dropwise, at about 0° to 5° C., whilst stirring. The solution, which initially is brown, becomes milky and turbid. After standing overnight at room temperature, a brown oil separates out and this is separated off and taken up in ether. The ethereal solution is extracted by shaking with water, the ether extract is dried and the ether is distilled off. A syrup remains as the residue and this become crystalline after some time. After recrystallisation from acetone, 46.5 g (69% of theory) of the tris-(2-hydroxyphenyl) ester of cyanuric acid, which has a melting point of 205° to 207° C., are obtained.

EXAMPLE 5

55 g of pyrocatechol are dissolved in 200 ml of water and, after passing nitrogen through the solution, 500 ml of N NaOH are added. 40 ml of cyanogen chloride are then added dropwise, from a cooled dropping funnel, at about 0° to 5° C., whilst stirring, and the mixture is left to stand overnight at room temperature. A brown oil separates out, which is separated off and taken up in ether. The ethereal solution is extracted by shaking with water, the ether extract is dried and the ether is distilled off. A syrup is obtained as the residue and this becomes crystalline after some time. After recrystallisation from acetone, 43 g (63.7% of theory) of the tris-(2-hydroxyphenyl) ester of cyanuric acid, which has a melting point of 205° to 207° C., are obtained.

EXAMPLE 6

84.5 g (0.5 mol) of 4-tert.-butylpyrocatechol are dissolved in a mixture of 500 ml of methylene chloride and 1,250 ml of water. 75 ml (1.5 mols) of cyanogen chloride are added to this solution at 0° C. Whilst cooling and stirring, 53 g (0.5 mol) of $Na_2CO_3$, dissolved in 200 ml of water, are then added dropwise, at a temperature between 0° and 10° C., at such a rate that a pH value of 8 is maintained. 700 ml of N NaOH are then added dropwise. After standing overnight at room temperature, the aqueous phase is separated off and the methylene chloride solution is evaporated to dryness. The residue is dissolved in hot ligroin; after adding petroleum ether, 81 g (84% of theory) of the tris-(tert.-butyl-2-hydroxyphenyl) ester of cyanuric acid, which has a melting point of 135° to 139° C., crystallise out.

EXAMPLE 7

22.2 g (0.1 mol) of 3,5-di-tert.-butylpyrocatechol are initially introduced into 200 ml of toluene and 11.1 g (0.105 mol) of triethylamine are added. The solution develops a dark blue coloration. Whilst stirring and cooling, 5.3 ml (0.105 mol) of cyanogen chloride are added dropwise at about 0° C. and the mixture is then stirred for a further 2 hours at room temperature. The toluene solution is worked up analogously to Example 1. The residue obtained after distilling off the toluene is recrystallised from toluene/ligroin; this gives 21.8 g (88% of theory) of the tris-(di-tert.-butyl-2-hydroxyphenyl) ester of cyanuric acid, which melts at 232° to 235° C.

The residue can also be recrystallised from ethanol with the addition of a little water.

EXAMPLE 8

22.2 g of 3,5-di-tert.-butylpyrocatechol are initially introduced into 200 ml of ligroin. After adding 5.3 ml of cyanogen chloride, 11.1 g of triethylamine are allowed to run in dropwise, whilst cooling and stirring, at about −5° C. The mixture is then stirred for a further 2 hours at room temperature. The triethylamine hydrochloride which has precipitated is eluted with a large amount of ligroin and the combined ligroin solutions are washed with water until free from chloride. After distilling off the ligroin, a yellowish-tinged syrup remains as the residue and this crystallises on prolonged standing at room temperature and is recrystallised from toluene/ligroin. This gives 22 g (89% of theory) of the tris-(di-tert.-butyl-2-hydroxyphenyl) ester of cyanuric acid, which has a melting point of 232° to 235° C.

EXAMPLE 9

16 g (0.1 mol) of 2,3-dihydroxynaphthalene are initially introduced into 100 ml of toluene. After adding 5.3 ml (0.105 mol) of cyanogen chloride, 11.1 ml (0.105 mol) of triethylamine are added dropwise, whilst cooling and stirring, at about −5° C. and the mixture is then stirred for about a further 2 hours. The precipitate which has separated out is filtered off and washed with a large amount of water until free from chloride. This gives 12.8 g (69% theory) of the tris-(3-hydroxynaphthyl-(2)) ester of cyanuric acid, which melts between 238° and 241° C.

EXAMPLE 10

80 g (0.5 mol) of 2,3-dihydroxynaphthalene are dissolved in 500 ml of methylene chloride and 1,250 ml of water. 75 ml (1.5 mols) of cyanogen chloride are added to this solution at 0° C. and subsequently 53 g (0.5 mol) of $Na_2CO_3$, dissolved in 200 ml of water, are added dropwise, whilst stirring and cooling in a temperature range of from 0° to 10° C., at such a rate that the pH value of the reaction mixture is kept at 7.5 to 8. A total of 700 ml of N NaOH is then added dropwise. A colourless precipitate separates out. When the reaction is complete, the mixture is left to stand overnight at room temperature and the reaction product is then filtered off and recrystallised from acetone. This gives 70 g (76% of theory) of the tris-(3-hydroxynaphthyl(2)) ester of cyanuric acid, which has a melting point of 238° to 241° C.

What is claimed is:

1. Process for preparing a tris-(2-hydroxyaryl) ester of cyanuric acid of the formula:

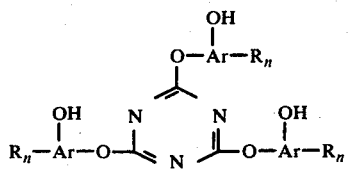

wherein

is a $C_6$–$C_{14}$ aromatic radical with a hydroxyl group in the 2-position to the ether oxygen, R is alkyl of up to 9 carbon atoms, phenyl, halogen, nitro, hydroxyl, alkoxy of up to 9 carbon atoms in the alkyl group or phenoxy, and n is 0 or 1 or is 2, 3 or 4 in which case one R has the above-defined meaning and each further radical R is alkyl having up to 9 carbon atoms, the radicals R optionally being different, which comprises reacting a 1,2-dihydroxyaryl compound of the formula:

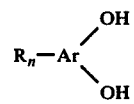

wherein

Ar is an aromatic radical and

R and n have the above defined meanings with cyanogen halide in the presence of a solvent and a hydrogen halide acceptor.

2. Process of claim 1 wherein R is alkyl.

3. Process of claim 1 carried out at temperatures between −40° C. and +65° C.

4. Process of claim 1 carried out at temperatures between −5° C. and +20° C.

5. Process of claim 1 wherein the solvent is water, a lower aliphatic alcohol, an aromatic hydrocarbon, an aliphatic chlorinated hydrocarbon or a mixture thereof.

6. Process of claim 5 wherein the solvent is toluene, methylene chloride, isopropanol, water, a mixture of isopropanol and water or a mixture of methylene chloride and water.

7. Process of claim 1 wherein the hydrogen halide acceptor is selected from tertiary amines, alkali metal hydroxides, alkaline earth metal hydroxides, alkali metal carbonates and alkaline earth metal carbonates.

8. Process of claim 7 wherein the hydrogen halide acceptor is selected from triethylamine and the hydroxides and carbonates of sodium and potassium.

9. Process of claim 1 wherein the cyanogen halide is cyanogen chloride.

* * * * *